United States Patent [19]

Cozzi et al.

[11] Patent Number: 4,882,347

[45] Date of Patent: Nov. 21, 1989

[54] "N-IMIDAZOLYL DERIVATIVES OF BICYCLIC COMPOUNDS AND PHARMACEUTICAL COMPOSITIONS CONTAINING THE SAME"

[75] Inventors: Paolo Cozzi, Milan; Corrado Ferti, Barlassina; Patricia Salvati, Arese; Germano Carganico; Antonio Pillan, both of Milan, all of Italy

[73] Assignee: Farmitalia Carlo Erba, S.r.l., Milan, Italy

[21] Appl. No.: 201,909

[22] Filed: Jun. 2, 1988

[30] Foreign Application Priority Data

Jun. 3, 1987 [GB] United Kingdom .................. 8712994
Jun. 3, 1987 [GB] United Kingdom .................. 8712995

[51] Int. Cl.$^4$ ............................................. A61K 31/415
[52] U.S. Cl. ..................................... 514/396; 514/397; 514/399; 514/866
[58] Field of Search ................ 514/396, 397, 399, 866

[56] References Cited

U.S. PATENT DOCUMENTS

| | | | |
|---|---|---|---|
| 3,992,403 | 11/1976 | Roebke | 514/866 |
| 4,492,707 | 1/1985 | Cozzi et al. | 514/399 |
| 4,510,149 | 3/1985 | Cozzi et al. | 514/866 |
| 4,588,738 | 5/1986 | Cozzi et al. | 514/399 |
| 4,602,022 | 7/1986 | Cozzi et al. | 514/337 |
| 4,634,705 | 1/1987 | De Bernardis et al. | 514/397 |

FOREIGN PATENT DOCUMENTS 2510113 7/1981 France .................. 514/397
2141705 3/1985 United Kingdom .

OTHER PUBLICATIONS

Cecil, "Textbook of Medicine", Sixteenth Edition, Saunders, (1982).
Whitley et al., "Acute Glomerulonephritis" Medical Clinics of North America-vol. 68, No. 2, Mar. 1984.
Am. J. Med. 64, 804–807 (1978)–Kimberly et al.
Kidney Intern. 30 (1986) 760-768–Toto et al.
Nephron 45 306–310 (1987)–Izumino et al.
Kidney Intern. 27, 189A (1985), Dworkin et al.
Hypertension & Glomerular Injury in Rats–J. Clin. Invest. 77 (1986), 1993–2000–Anderson, now Eng. J. Med. 296(8)–418-424 (1977) Kimberly et al.

Primary Examiner—Douglas W. Robinson
Attorney, Agent, or Firm—Oblon, Spivak, McClelland, Maier & Neustadt

[57] ABSTRACT

A pharmaceutical compositon having activity against nephropathies comprising, as an active agent, a therapeutically effective amount of a compound of formula (I)

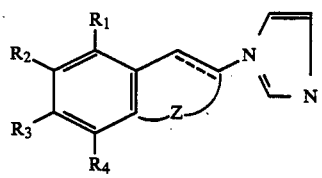

wherein
(a)

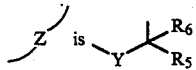

wherein Y completes a single bond or is oxygen or a —CH$_2$— group and the symbol ==== represents a single or a double bond or (b)

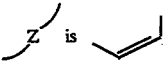

and the symbol represents a double bond; one of R$_1$, R$_2$, R$_3$ and R$_4$ is —CH$_2$OH, C$_2$–C$_4$ acyl,

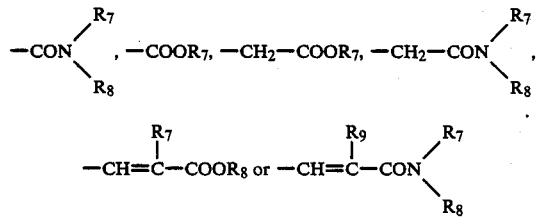

in which each of R$_1$, R$_8$ and R$_9$ is independently hydrogen or C$_1$–C$_4$ alkyl and the others are independently chosen from hydrogen, hydroxy, halogen, C$_1$–C$_4$ alkyl, C$_1$–C$_4$ alkoxy and —COOR, wherein R$_7$ is as defined above, and one of R$_5$ and R$_6$ is hydrogen and the other is hydrogen, C$_1$–C$_6$ alkyl or phenyl; or a pharmaceutically acceptable salt thereof; and a pharmaceutically acceptable carrier and/or diluent.

5 Claims, No Drawings

"N-IMIDAZOLYL DERIVATIVES OF BICYCLIC COMPOUNDS AND PHARMACEUTICAL COMPOSITIONS CONTAINING THE SAME"

This invention relates to the use of N-imidazolyl derivatives of bicyclic compounds in a method of treating nephropathies in mammals and to pharmaceutical compositions containing the same for such use.

DESCRIPTION OF THE BACKGROUND

N-imidazolyl derivatives containing a naphthalene, indene or chroman nucleus, and the pharmaceutically acceptable salts thereof, are described in US-A-4,510,149 and in BG-B-2,141,705. They are known to exhibit pharmaceutical activity, in particular as vasodilators or blood platelet aggregation inhibitors. Additionally, these compounds, and their pharmaceutically acceptable salts, are known to be useful in the treatment of migraine, diabetic microangiopathy, rheumatoid arthritis, hypertension, peptic ulcers, osteoporosis, angina pectoris, atherosclerosis and dislipidaemias. At present, however, the utility of these compounds in the treatment of nephropathies, where remains a strong need for new therapeutical agents, has never been described before.

SUMMARY OF THE INVENTION

Accordingly, it is an object of the present invention to provide pharmaceutical compositions which are active against nephropathies, containing, as an active agent, a therapeutically effective amount of a compound of the formula (I)

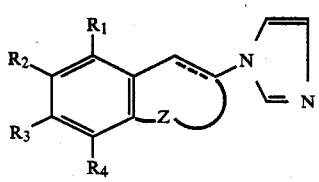

wherein
(a)

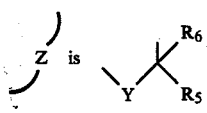

wherein Y completes a single bond or is oxygen or a —$CH_2$— group and the symbol

═ represents a single or a double bond or (b)

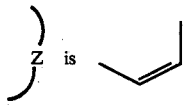

and the symbol

═ represents a double bond; one of $R_1$, $R_2$, $R_3$ and $R_4$ is —$CH_2OH$, $C_2$–$C_4$ acyl,

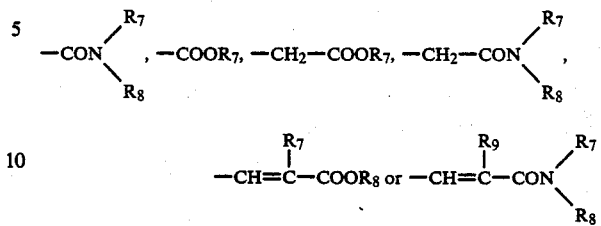

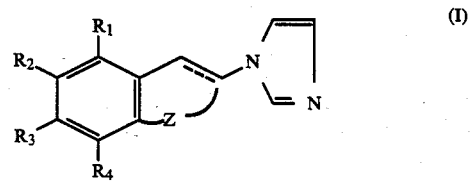

in which each of $R_7$, $R_8$ and $R_9$ is independently hydrogen or $C_1$–$C_4$ alkyl and the others are independently chosen from hydrogen, hydroxy, halogen, $C_1$–$C_4$ alkyl, $C_1$–$C_4$ alkoxy and —$COOR_7$ wherein $R_7$ is as defined above, and one of $R_5$ and $R_6$ is hydrogen and the other is hydrogen, $C_1$–$C_6$ alkyl or phenykl; or a pharmaceutically acceptable salt thereof, and a pharmaceutically acceptable carrier and/or diluent.

DETAILED DESCRIPTION OF THE PREFERRED EMBODIMENTS

In accordance with the present invention, it has now been found that certain compounds having the formula (I), which are described in U.S. Pat. No. 4,510,149 and British Pat. No. 2,141,705,

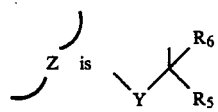

wherein
(a)

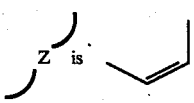

wherein Y completes a single bond or is oxygen or a —$CH_2$— group and the symbol

═ represents a single or a double bond or (b)

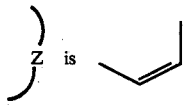

and the symbol

═ represents a double bond; one of $R_1$, $R_2$, $R_3$ and $R_4$ is —$CH_2OH$, $C_2$–$C_4$ acyl,

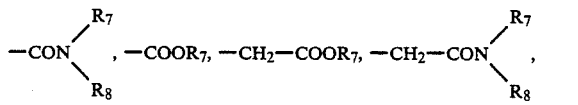

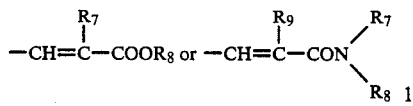

in which each of $R_7$, $R_8$ and $R_9$ is independently hydrogen or $C_1$-$C_4$ alkyl and the others are independently chosen from hydrogen, hydroxy, halogen, $C_1$-$C_4$ alkyl, $C_1$-$C_4$ alkoxy and —$COOR_7$ wherein $R_7$ is as defined above, and one of $R_5$ and $R_6$ is hydrogen and the other is hydrogen, $C_1$-$C_6$ alkyl or phenyl; or a pharmaceutically acceptable salt thereof, are useful for the treatment, in mammals, of nephropathies, as e.g. some forms of glomerulonephritis, microalbuminuria in diabetic patients or nephropathies secondary to systemic lupus eruthematosus (SLE), and of hyperlipidaemias, namely hypercholesterolaemias and hypertriglyceridaemias, secondary to nephrotic syndrome. Among the compounds disclosed by U.S. Pat. No. 4,510,149 and British Pat. No. 2,141,705 only those having a

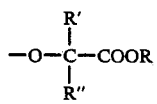

group, wherein each of R, R' and R" independently is hydrogen or $C_1$-$C_6$ alkyl, are endowed with high activity in lowering cholesterol and triglycerides, in increasing the total serum HDL cholesterol, as well as in increasing the ratio between α-lipoprotein and β-lipoprotein total cholesterol.

As is known, drugs having such activities are useful in prevention and therapy of atherosclerosis: Glueck C. J., Artery, 2, 196 (1976); Day C. E. in Frank-H-Clarke (Ed.) Annual reports in Medicinal Chemistry, 13, 184, chapter 2-Academic Press, N.Y. 1978. Therefore it is, indeed, surprising that the compounds of formula (I), according to the present invention, and the pharmaceutically acceptable salts thereof, are active in lowering elevated plasma levels of both total cholesterol and triglycerides in patients with nephropathy.

Preferred compounds of formula (I) are those wherein Z is

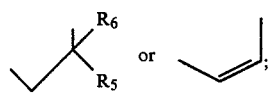

one of $R_1$, $R_2$, $R_3$ and $R_4$ is —$CH_2OH$, $C_2$-$C_4$ acyl,

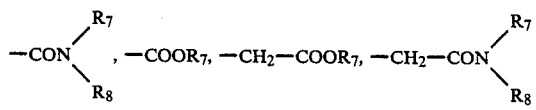

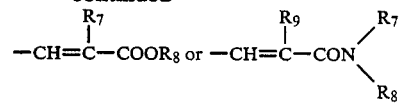

in which each of $R_7$, $R_8$ and $R_9$ is independently hydrogen or $C_1$-$C_4$ alkyl and the others are hydrogen and $R_5$ and $R_6$ are hydrogen; and the pharmaceutically acceptable salts thereof.

Examples of preferred compounds of formula (I) are the following:

1,2-dihydro-3-(1-imidazolyl)-6-carboxynaphthalene;
1,2-dihydro-3-(1-imidazolyl)-6-ethoxycarbonylnaphthalene;
1,2-dihydro-3-(1-imidazolyl)-6-hydroxymethylnaphthalene;
1,2-dihydro-3-(1-imidazolyl)-7-carboxynaphthalene;
1,2-dihydro-3-(1-imidazolyl)-6-(2-carboxyvinyl)-naphthalene;
1,2-dihydro-3-(1-imidazolyl)-6-(2-ethoxycarbonylvinyl)naphthalene;
1,2-dihydro-3-(1-imidazolyl)-6-carboxymethylnaphthalene;
1,2,3,4-tetrahydro-2-(1-imidazolyl)-7-carboxynaphthalene;
2-(1-imidazolyl)-7-carboxynaphthalene;
2-(1-imidazolyl)-6-carboxynaphthalene;

and the pharmaceutically acceptable salts thereof and, when appropriate, the $C_1$-$C_4$ alkyl esters thereof.

Pharmaceutically acceptable salts of the compounds of formula (I) include acid addition salts, with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, citric, benzpoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethylamine. The alkyl and alkoxy groups may be branched or straight chain groups.

A halogen atom is, for example, fluorine, chlorine or bromine, preferably chlorine or bromine.

A $C_1$-$C_4$ or -$C_6$ alkyl group is preferably methyl or ethyl.

A $C_1$-$C_4$ alkoxy group is preferably methoxy or ethoxy.

As stated above, the compounds of formula (I), as well as the preferred ones hereabove specifically mentioned, are already described in U.S. Pat. No. 4,510,149 and GB Pat. No. 2,141,705. The details inherent to the methods of their preparation are described in the above-identified U.S. and British patents.

U.S. Pat. No. 4,510,149 is incorporated herein by reference in the entirety.

The compounds of formula (I), as stated above, are useful for the treatment of nephropathies in mammals, especially humans, as shown e.g. by the fact that they have proved to be active in reducing proteinuria and creatinine serum levels in the doxorubicin induced nephrosis in rats and in reducing proteinuria and increasing the glomerular filtration rate (GFR) in spontaneous focal glomerulonephritis in the Milan Normotensive Strain (MNS) rats.

The present invention will now be further illustrated by certain examples and references which are provided for purposes of illustration only and are not intended to limit the present invention.

EXAMPLE 1

The compound 1,2-dihydro-3-(1-imidazolyl)-6-carboxy-naphthalene (internal code FCE 22178) was orally administered, for doxorubicin induced nephrosis, to rats at a dosage of 50 mg/kg b.i.d. for 7 days starting from the 21st day after doxorubicin injection. A reduction in both proteinuria (from $1018 \pm 102$ to $751 \pm 49$ mg/24 h $p<0.005$) and creatinine serum levels (from $1.85 \pm 0.26$ to $0.97 \pm 0.009$ mg/dl $p<0.001$) was observed.

This effect was paralleled by significant inhibition of both serum and urine $TxB_2$ levels: serum levels were reduced from $536 \pm 55$ ng/ml to $92 \pm 8.3$ ng/ml and urine levels from $20.3 \pm 2.5$ ng/24 h to values under the detection limit of the method. Moreover, in the spontaneous focal glomerulonephritis of the MNS rats, FCE 22178 was administered at the dosage of 50 mg/kg p.o. die + 100 mg/kg/die in drinking water starting from the first month of age and all along the life of the animal and in comparison with a not treated group. During the development of the disease MNS rats showed an increased production of $TxA_2$ (measured as $TxB_2$ levels) in isolated glomeruli ($4.44 \pm 1.2$ ng/mg prot. $p<0.01$ at 8 months of age) which was greatly reduced by FCE 22178 ($2.77 \pm 0.53$ ng/mg prot. $p<0.01$). The same pattern was observed in urine. In adult control MNS rats a progressive increase in proteinuria paralleled by a decrease in GFR was also observed: FCE 22178 treatment reduced proteinuria ($237 \pm 30.3$ vs $428.8 \pm 42.3$ mg/24 h $p<0.01$) and increased GFR towards normal values ($1210 \pm 38$ in controls vs $816 \pm 45$ $\mu$l/min/g k.w. in treated rats $p<0.01$).

Histological evaluation

Light microscopy of the kidneys of aged (14 months) control MNS rats revealed that 27% of the glomeruli display an increase in mesangial matrix and segmental glomerulosclerosis. Sclerotic glomeruli show massive deposition of PAS-stained material.

Ultrastructural investigation of non sclerotic glomeruli showed that an age-related process takes place in MNS rats; in particular, the thickening of the glomerular basement membrane (GMB) and the increase in mesangial matrix appear to be strictly related to the structural modifications of the epithelial cells. Flattening and fusion of the foot processes, as well as formation of blebs and of electron dense lysosomes, together with the frequent detachment of the cell from the GMB is regarded to be related to the massive leakage of proteins through the glomerulus. Treatment for example with compound FCE 22178 significantly ($p<0.05$) reduced the number of sclerotic glumeruli (22%). More impressive and relevant were the ultrastructural differences between treated and untreated animals in non sclerotic glomeruli: the entity of flattening and fusion of foot processes was found to be definitly lower in treated animals, pointing to a significant effect of the treatment in preventing the full picture typical of untreated MNS rats.

The activity of compound FCE 22178, for example, was evaluated also in the model of subtotal renal ablation in the rat. This model as known results in proteinuria, hypertension and progressive kidney disease. Rats with a remnant kidney (RRM) have increased excretion in the urine and glomerular production of Thromboxane $B_2$ ($TxB_2$).

Methods

Charles River C.D. male rats of 6 weeks of age were used for this experiment. The left kidney was surgically reduced for the 60% and one week later the right kidney was removed. Four weeks after the second operation the blood pressure was measured and the rats were placed in metabolic cages for evaluation of proteinuria, measured by the method of Lowry. Only the animals with a blood pressure $\geq 170$ mm Hg and an urinary protein excretion $\geq 100$ mg/day were used. Comparative experiments were performed using sham operated rats. Also the in vitro $TxA_2$ synthase inhibiting activities in serum and in isolated glomeruli were studied and compared. Glomerula preparation was performed according to the method previously described and $TxB_2$ was measured by RIA.

Compound FCE 22178 was tested at concentrations ranging from $4 \times 10^{-12}$M to $2 \times 10^{-8}$M. For comparison purposes the well known thromboxane synthase inhibition (E)-3-[4-(1H-imidazol-1-ylmethyl)-phenyl]-2-propenoic acid monohydrochloride monohydrate, coded as OKYO46 and disclosed by U.S. Pat. No. 4,226,878, was tested at the same concentrations.

Results

Compound FCE 22178 showed a greater activity in inhibition glomerular than serum $TxB_2$ production in RRM rats: the $IC_{50}$ were $3.2 \times 10^{-11}$M in glomeruli and $1.7 \times 10^{-9}$M in serum.

Compound OKYO46 showed a slightly greater potency in inhibiting serum $TxA_2$ synthesis: $IC_{50}$ $6 \times 10^{-10}$M, but a lower activity on glomeruli as compared to compound FCE 22178: $IC_{50}$ $9 \times 10^{-11}$M. These results indicate compound FCE 22178 possesses a greater selectivity for glomerular $TxA_2$ synthase as compared to compound OXYO46. This fact is even more evident in control sham operated rats, where compound FCE 22178 maintained a greater activity in glomeruli: $IC_5 7 \times 10^{-11}$M vs. $1 \times 10^{-9}$M in serum, whereas compound OKYO46 losed his selectivity: $IC_{50} 1 \times 10^{-9}$ in glomeruli vs. $5 \times 10^{-5}$M in serum.

The compounds of formula (I), as stated above, are also useful for the treatment of hyperlipidaemias secondary to nephrotic syndrome as shown e.g. by the fact that they have proved to be active in reducing cholesterol, triglycerides and phospholipids in aged Milan Normotensive Strain (MNS) rats and in reducing triglycerides in doxorubicin treated rats. On the other hand hyperlipidemia is characteristic of the nephrotic syndrome: elevated plasma levels of both total cholesterol and triglycerides have been reported in patients with nephropathy (Appel G. B. et al.—New England J. Med. 312, 24, 1544, 1985 and Chopra J. S. et al.—Lancet Feb. 1, 317, 1971). This metabolic disorder can be reproduced in doxorubicin induced nephrosis (Calandra S. et al.—Exp. Mol. Pathology 39, 282, 1983).

Compound 1,2-dihydro-3-(1-imidazolyl)-6-carboxynaphthalene, internal code FCE 22178, for instance, in this model at the oral dosage of 50 mg/kg b.i.d. for 7 days starting from the 21st after doxorubicin injection lowered triglycerides serum levels from $783 \pm 152$ to $481.8 \pm 84$ mg/dl.

Also in spontaneous glomerulonephritis of MNS rats this metabolic disorder is present and FCE 22178 was very active in ameliorating the disease: in fact in this model the product lowered, in 14 months old rats treated for 2 months, total cholesterol from $223 \pm 36$ to $130.5 \pm 12.2$ mg/dl, triglycerides from $399.6 \pm 105$ to $169.3 \pm 26.1$ mg/dl and phospholipids from $338.6 \pm 56$ to $197.8 \pm 21$ mg/dl.

The toxicity of the compounds of the invention is negligible, therefore they can be safely used in therapy. Mice and rats which had been deprived of food for nine hours were treated orally with single administrations of increasing doeses of compounds of the invention, then housed and normally fed. The orientative acute toxicity ($LD_{50}$) was assessed on the seventh day after the treatment and was higher than 800 mg/kg.

In view of their high therapeutic index the compounds of formula (I) can be safely used in medicine. The dosage level suitable for oral administration to adult humans of the compounds of formula (I), e.g. 1,2-dihydro-3-(1-imidazolyl)-6-carboxy-naphthalene, may range from about 100 mg to about 800 mg per dose 1 to 3 times a day, preferably from about 200 mg to about 400 mg per dose 1 to 3 times a day. The exact dosage depends on the disease, age, weight, condition of the patient and administration route.

The compounds can be administered in a variety of dosage forms, e.g., orally, in the form of tablets, capsules, sugar, or film coated tablets, liquid solutions or suspensions; rectally, in the form of suppositories; parenterally, e.g. intramuscularly; or by intravenous injection or infusion. The invention includes pharmaceutical compositions comprising a compound of formula (I) in association with a pharmaceutically acceptable excipient (which can be a carrier or diluent). The pharmaceutical compositions can be usually prepared following conventional methods and administered in a pharmaceutically suitable form.

For example, the solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating processes.

The liquid dispersions for oral administration may be e.g. syrups, emulsions, and suspensions. The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g., propylene glycol, and if desired, a suitable amount of lidocaine hydrochloride. The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following additional examples are provided also for illustration and are not intended to limit the present invention.

EXAMPLE 2

Tablets, each weighing 300 mg and containing 100 mg of the active substance can be manufactured as follows:

| Compositions (for 10,000 tablets) | |
|---|---|
| 1,2-dihydro-3-(1-imidazolyl)-6-carboxynaphthalene | 1000 g |
| lactose | 1420 g |
| corn starch | 475 g |
| talc powder | 75 g |
| magnesium stearate | 30 g |

1,2-dihydro-3-(1-imidazolyl)-6-carboxy-naphthalene, lactose and a half of the corn starch are mixed; the mixture is then forced through a sieve of 0.5 mm openings. Corn starch (36 mg) is suspended in warm water (350 ml). The resulting paste is used to granulate the powder. The granules are dried, comminuted on a sieve of sieve size 1.4 mm, then the remaining quantity of starch, talc and magnesium are added, carefully mixed, and processed into tablets using punches of 10 mm diameter.

EXAMPLE 3

Intramuscular injection

An injectable pharmaceutical composition can be manufactured by dissolving 100 mg of 1,2-dihydro-3-(1-imidazolyl)-6-carboxynaphthalene sodium salt in sterile water or sterile normal saline solution (1–2 ml).

EXAMPLE 4

Capsules (100 mg)

| | |
|---|---|
| 1,2-dihydro-3-(1-imidazolyl)-6-carboxynaphthalene | 100 mg |
| lactose | 248 mg |
| corn starch | 50 mg |
| magnesium stearate | 2 mg |
| Total | 400 mg |

Encapsulate in two-piece hard gelatine capsules.

EXAMPLE 5

Suppository (100 mg)

| | |
|---|---|
| 1,2-dihydro-3-(1-imidazolyl)-6-carboxynaphthalene | 0.10 g |
| lecithin | 0.14 g |
| cocoa butter | 1.76 g |
| Total | 2.00 g |

What is claimed as new and desired to be secured by Letters Patent of the United States is:

1. A method of treating nephropathies in mammals, said nephropathies being selected from the group consisting of glumerulonephritis, nephropathy secondary to lupus erithematosus, and hyperlipidaemias secondary to nephrotic syndrome, which comprises administering to said mammals an effective amount of a pharmaceutical composition comprising:
   (a) a therapeutically effective amount of a compound of the formula (I):

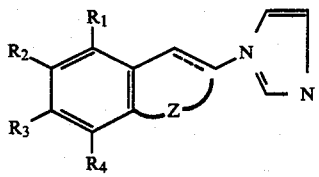 (I)

wherein
(I) —Z— is:

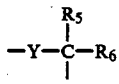

wherein Y completes a single bond or is oxygen or a —CH$_2$— group and the symbol:

represents a single or a double bond, or
(II) —Z— is:

and the symbol:

represents a double bond; one of R$_1$, R$_2$, R$_3$, R$_4$ is —CH$_2$OH, C$_2$–C$_4$ acyl, —CONR$_7$R$_8$, —COOR$_7$, —CH$_2$—COOR$_7$, —CH$_2$CONR$_7$R$_8$, —CH═C(R$_7$)—COOR$_8$ or —CH═C(R$_9$)—CONR$_7$R$_8$ in which each of R$_7$, R$_8$ and R$_9$ is independently hydrogen or C$_1$–C$_4$ alkyl and the others are independently selected from the group consisting of hydrogen, hydroxy, halogen, C$_1$–C$_4$ alkyl, C$_1$–C$_4$ alkoxy and —COOR$_7$, wherein R$_7$ is as defined above, and one of R$_5$ and R$_6$ is hydrogen and the other is hydrogen, C$_1$–C$_6$ alkyl or phenyl; and
(b) a pharmaceutically acceptable carrier.

2. The method of claim 1, wherein in the compound of formula (I):
—Z— is

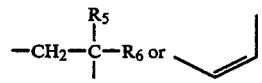

one of R$_1$, R$_2$, R$_3$ and R$_4$ is —CH$_2$OH, C$_2$–C$_4$ acyl, —CONR$_7$R$_8$, —COOR$_7$, —CH$_2$—COOR$_7$, —CH$_2$—CONR$_7$R$_8$, —CH═C(R$_7$)—COOR$_8$ or —CH═C(R$_9$)COONR$_7$R$_8$, in which R$_7$, R$_8$ and R$_9$ is independently hydrogen or C$_1$–C$_4$ alkyl and the others are hydrogen, and R$_5$ and R$_6$ are hydrogen.

3. The method of claim 1, wherein said compound of formula (I) is 1,2-dihydro-3-(1-imidazolyl)-6-carboxynaphthalene.

4. The method of claim 1, wherein said compound of the formula (I) is selected from the group consisting of:
1,2-dihydro-3-(1-imidazolyl)-6-ethoxycarbonylnaphthalene;
1,2-dihydro-3-(1-imidazolyl)-6-hydroxymethylnaphthalene;
1,2-dihydro-3-(1-imidazolyl)-7-carboxynaphthalene;
1,2-dihydro-3-(1-imidazolyl)-6-(2-carboxyvinyl)-naphthalene;
1,2-dihydro-3-(1-imidazolyl)-6-(2-ethoxycarbonylvinyl)naphthalene;
1,2-dihydro-3-(1-imidazolyl)-6-carboxymethylnaphthalene;
1,2,3,4-tetrahydro-2-(1-imidazolyl)-7-carboxynaphthalene;
2-(1-imidazolyl)-7-carboxynaphthalene; and
2-(1-imidazolyl)-6-carboxynaphthalene.

5. The method of claim 1, wherein said hyperlipidaemias secondary to nephrotic syndrome are hypercholesterolaemia secondary to nephrotic syndrome and hypertriglyceridaemia secondary to nephrotic syndrome.

* * * * *